United States Patent
Korpi

(10) Patent No.: US 7,285,736 B2
(45) Date of Patent: Oct. 23, 2007

(54) OSCILLATING INERTIAL MICROBALANCE AND METHOD OF PASSIVE COMPENSATION

(76) Inventor: David Michael Korpi, 22642 Indian Springs Rd., Salinas, CA (US) 93908

( * ) Notice: Subject to any disclaimer, the term of this patent is extended or adjusted under 35 U.S.C. 154(b) by 0 days.

(21) Appl. No.: 10/904,074

(22) Filed: Oct. 21, 2004

(65) Prior Publication Data

US 2006/0086174 A1    Apr. 27, 2006

(51) Int. Cl.
*G01G 3/16* (2006.01)
(52) U.S. Cl. .............................................. 177/210 FP
(58) Field of Classification Search .......... 177/210 FP, 177/201, 210 R; 73/580
See application file for complete search history.

(56) References Cited

U.S. PATENT DOCUMENTS 5,604,335 A * 2/1997 Isahaya ................. 177/210 FP
6,205,842 B1 * 3/2001 Patashnick et al. ......... 73/28.01
6,444,927 B1 * 9/2002 Korpi ..................... 177/210 FP \* cited by examiner

*Primary Examiner*—Randy W. Gibson
*Assistant Examiner*—Sean Kayes

(57) ABSTRACT

The claimed subject matter is directed to a continuous passive temperature, pressure, modulus of elasticity, and force compensated oscillating inertial microbalance and method of using the same. Temperature and/or pressure and/or modulus of elasticity compensation and/or force compensation is achieved by providing two substantially similar oscillating elements wherein only one oscillating element is subjected to the particulate collection means. The other oscillating element is subjected to all other factors but does not include a particulate collection means. By taking the difference between the two similar oscillating elements one can substantially remove the undesirable side effects having to do with changing temperature and/or pressure and/or modulus of elasticity. The ratio of the major axis to the minor axis is important to minimize precession of the oscillating elements.

12 Claims, 4 Drawing Sheets

$$m = \frac{\text{Bulk K}}{\text{abs}[f1^2 - f2^2]}$$

Ratio of Major Axis to Minor Axis > 1.5:1 or Y > 1.5(X)

OSCILLATING INERTIAL MICROBALANCE AND METHOD OF PASSIVE COMPENSATION

BACKGROUND OF INVENTION

This invention relates to oscillating inertial microbalance mass measurement devices and, more specifically, to mass measurement devices that reduce the adverse effects that temperature, pressure, force, and modulus of elasticity have on the true indication of mass. It is known in the art that vibrating systems have a large dependency on their environment, materials of construction, and method of manufacturing.

A significant contribution to the adverse effects can come from a non-ideal oscillating element that is at the heart of the classical oscillating inertial microbalance. Exemplary construction and operation of such oscillating inertial microbalance mass measurement devices are disclosed in U.S. Pat. Nos. 4,391,338, 6,444,927, and 6,784,381 which patents hereby are incorporated herein by reference in their entirety.

An ideal oscillating element is one that has the ability to indicate the mass of the collected matter without the need to compensate for external outside acting forces such as temperature, pressure, modulus of elasticity, external vibration or any other force that may create an adverse effect on the true indication of the mass.

For instance, a non-ideal oscillating element can exhibit a change in the modulus of elasticity with temperature. It is difficult to precisely determine how to apply corrections for temperature when the adverse effects are comprised of those from the fluid properties of the sampled gas and those errors contributed by a change in the modulus of elasticity of the oscillating element has with temperature.

The problems associated with maintaining the gas stream and the oscillating element at a constant temperature are discussed in U.S. Pat. No. 6,080,939 and methods for controlling the same are discussed in U.S. Pat. No. 6,444,927

Further, instruments used to measure a particular parameter may be affected by the variation of other parameters. For example, measurement of the mass of material deposited on an oscillating inertial microbalance may be adversely affected by a variation in temperature and/or pressure and/or changes in modulus of elasticity of the oscillating element of the oscillating inertial microbalance.

A microbalance, examples of which are described in U.S. Pat. Nos. 3,926,271 and 4,391,338, typically comprises an oscillating element mounted with one end fixed and the other end free. The free end typically has a filter (or other mass-receiving element) mounted thereto.

When a microbalance is configured with a hollow oscillating element, the fluid is typically drawn through the filter and through the oscillating element, thereby trapping suspended particles within the fluid in or on the filter.

The resulting increase in the mass of the filter results in a decrease of the resonant frequency of the oscillating element. The decrease in the resonant frequency of the oscillating element is related to the increase in mass of the filter, which in turn is representative of the mass of the suspended particles trapped in or on the filter.

Because the oscillating element has the ability to continually indicate the mass of the suspended particles it is an ideal means for indicating the change in mass of the suspended particles trapped in or on the filter in near real time or over a measured period of time.

A microbalance, an example of which is described in U.S. Pat. No. 6,205,842, attempts to address the problem of the adverse mass indication as a result of the volatile components in the sample stream. The adverse mass indication is compensated for by having two substantially similar mass detectors where a particulate removal means is provided on one of the mass sensors to which the other is compared. A switching means is provided and equations are utilized to remove said adverse effects, enabled by the use of the switching means.

An attempt to remove the mechanical complexity of the switching means mentioned above is noted in U.S. Pat. No. 6,502,450, wherein only one sensor is used with the same particle removing means in a single flow path. The switching of a particle removal means and associated timing gives rise to the apparent loss in mass by using a formula. A further improvement of this patent, or a simplification to remove the adverse effects of volitization of the gas, is described in U.S. Pat. No. 6,651,480.

The goal of the three aforementioned patents is to address the adverse effects created by gas volitization in an inertial microbalance. They are not designed to remove the sensitivities an inertial microbalance has to the modulus of elasticity with temperature and the density change within the hollow oscillating element as a result of temperature and pressure. None of these patents provide for a continuous indication of the mass in near real time. Instead, they require that the particulate laden sample stream be interrupted, results in the disruption of the sampling cycle which can in turn potentially lead to the missing of an episode wherein a large concentration of the particulate sample is ignored.

Additionally, as the temperature of the microbalance's oscillating element changes, the resonant frequency of the oscillating element may change, even though the mass in or on the filter secured to the oscillating element may remain unchanged. As the measured mass is based on the resonant frequency, an error is introduced in the mass determination. This temperature sensitivity results primarily from a change in the modulus of elasticity of the materials from which the oscillating element is made. One way of addressing the concern of the temperature sensitivity of the microbalance, or other instrument, is to select a material of construction that has minimal sensitivity to changes in temperature.

For a microbalance, great care can be applied to the formulation of the material from which the oscillating element is made to attain the desired characteristics while attempting to optimize manufacturability and minimize the temperature sensitivity of the desired variables.

In particular, one way of reducing the temperature sensitivity of the microbalance known in the prior art is to use a shaped oscillating element made of a material having a low temperature coefficient of elastic modulus. In the end, compromises must be made at the expense of the accuracy, manufacturability and cost of the entire system.

U.S. Pat. No. 4,836,314 describes the selection of a material for an oscillating element fabricated from a glass of a specific composition. Additionally, U.S. Pat. No. 6,080,939 describes a process of heat treatment and material combination of a metallic material. Both of these patents fail to completely address the adverse effects of temperature sensitivity having to do with the modulus of elasticity of the oscillating element.

A method of compensation of adverse effects is described in U.S. Pat. No. 5,604,335 wherein the mass is only measured when the system is in a quiescent state wherein no flow is delivered to the oscillator. The dual sensor system fails to subject both oscillators to substantially the same conditions. Our invention specifically prescribes that both oscillators be subjected to substantially the same conditions.

U.S. Pat. No. 4,836,314 teaches a method of selection of the material of construction for reducing the thermal coefficient of elastic modulus over a selected temperature range. The patent shows a "recipe" for a glass alloy to accomplish a fairly low thermal coefficient of elastic modulus. It is important to note that a "fairly low" thermal coefficient of elastic modulus is not sufficiently "low" enough to support the resolution and accuracy demands that are the object of this invention.

U.S. Pat. No. 6,080,939 teaches a similar method of material selection and or treatment for a metallic oscillating element construction. It should be noted that the methods described in U.S. Pat. No. 6,080,939 are well known in the art of the manufacture of bourdon tube pressure gages and precision mechanical resonating structures, precision springs, tuning forks, vibration based pressure transducers, vibrating densitometers, and other precision elastic components.

Nearly every high quality mechanical bourdon tube type pressure gage, Heise, Aschcroft, Rosemount, and others utilize materials and procedures very similar to those discussed in U.S. Pat. No. 4,836,314.

U.S. Pat. Nos. 3,946,615 and 4,048,846 detail methods of addressing the thermal coefficient of elastic modulus with specific heat treatment methods with materials similar to Ni-Span-C. The now public manufacturing methods, from 1959, for the Bulova "Accutron" watch, that utilized a mechanical tuning fork, required materials and procedures similar to those discussed in U.S. Pat. Nos. 3,946,615 and 4,048,846 as well.

A vibrating level detection system for the indication of pressure including the compensation of the thermal coefficient of the elastic modulus are described in U.S. Pat. No. 4,311,053. It should be noted that this device actually takes advantage of the change in the resonant frequency of the system with pressure.

U.S. Pat. No. 6,502,450 states in part that "[t]o compensate for instrument effects in direct mass measurements, a differential particulate mass measurement microbalance employing a pair of oscillating quartz crystal detectors has previously been proposed."

In this previously proposed approach, a particle laden gas stream impacts upon the first detector and a particle free gas stream impacts the second detector. The second mass detector is used as a reference to cancel out detector instrument effects from a mass reading provided by the first detector. However, the first and second detectors are not of a geometry capable of addressing the additional problem of the density change of the fluid within the hollow oscillating element and therefore can not compensate for these effects. Additionally, the idea of impacting a clean and particulate laden gas stream requires removing particulate from one stream and leaving the other stream intact. This scheme requires a second particulate collection means. The subject invention, however, does NOT require a second particulate collection means.

U.S. Pat. No. 5,571,945 discloses a similar measurement approach employing a pressure sensor to measure a pressure differential between a pair of particulate matter collectors. This patent also requires removing particulate from one stream and leaving the other stream intact. Additionally, this scheme requires a second collection means.

Neither of these two aforementioned patents adequately addresses the adverse effects of indicating a mass because both subject the "reference" resonator to a change in state resulting from the collection of a "clean" sample.

U.S. Pat. No. 5,349,844 discloses a similar approach for use with a filter that is caused to oscillate in a direction substantially perpendicular to a plane of the filter.

SUMMARY OF INVENTION

One of the embodiments of the present invention is directed to an oscillating inertial microbalance comprising: a base; two elastic oscillating elements substantially equal in properties mounted at one end of said base; an enclosure; a means for exiting said oscillating elements; a means for measuring the resulting vibrations and a filter; wherein the mass of a particulate collected on the filter is measured by performing the steps of: forcing said oscillating elements into resonance, measuring the frequency of each of said oscillating elements, and comparing the results of the data derived from each said measurement. Another embodiment of the present invention is directed to an oscillating inertial microbalance wherein said oscillating elements are selected from the following group: nickel alloys, Ni-Span-C, Ni-Span-D, Inconel, quartz, and quartz-glass alloys. Another embodiment of the present invention is directed to an oscillating inertial microbalance wherein the elastic oscillating elements have a ratio of the major and minor diameters of at least 1.5:1 to minimize precession. Another embodiment of the present invention is directed to an oscillating inertial microbalance wherein the data derived from the pressure, temperature and acceleration are measured. Another embodiment of the present invention is directed to an oscillating inertial microbalance wherein said two elastic oscillating elements are not equal but have a known relationship to each other. In any system, where one wishes to remove "common mode" noise errors, it is not uncommon to utilize mechanical elements of differing sizes or characteristics as long as there can be found a constant relationship between them. As such it should be obvious to one skilled in mechanics that one could utilize elastic oscillating elements that differ in physical size but behave in a known manner compared to the elastic oscillating element responsible for collecting the mass. With this we can even see that one of the elements could be micro machined as indicated in U.S. Pat. No. 6,444,927 and U.S. Pat. No. 6,784,381.

Further, the two elastic oscillating elements can be mounted in such a way as to minimize energy transfer from one elastic oscillating element to the other elastic oscillating element. Consider two elastic oscillating elements mounted in the same plane as compared to those oscillating in orthogonal planes. It will be clear to those skilled in the art that an orthogonally mounted system will minimize the energy transfer between the two elastic oscillating elements.

Another embodiment of the present invention is directed to a method of operating a microbalance, the microbalance including two inertial oscillating elements with substantially equal properties and with at least one having a filter mounted at one end thereof, the method comprising: inducing resonance in said oscillating elements; measuring the frequency of each of said oscillating elements; and comparing the results of the data derived from each said measurement.

BRIEF DESCRIPTION OF DRAWINGS

Exemplary embodiments of the invention will now be described with reference to the attached drawings, in which.

DETAILED DESCRIPTION

Figure 1:
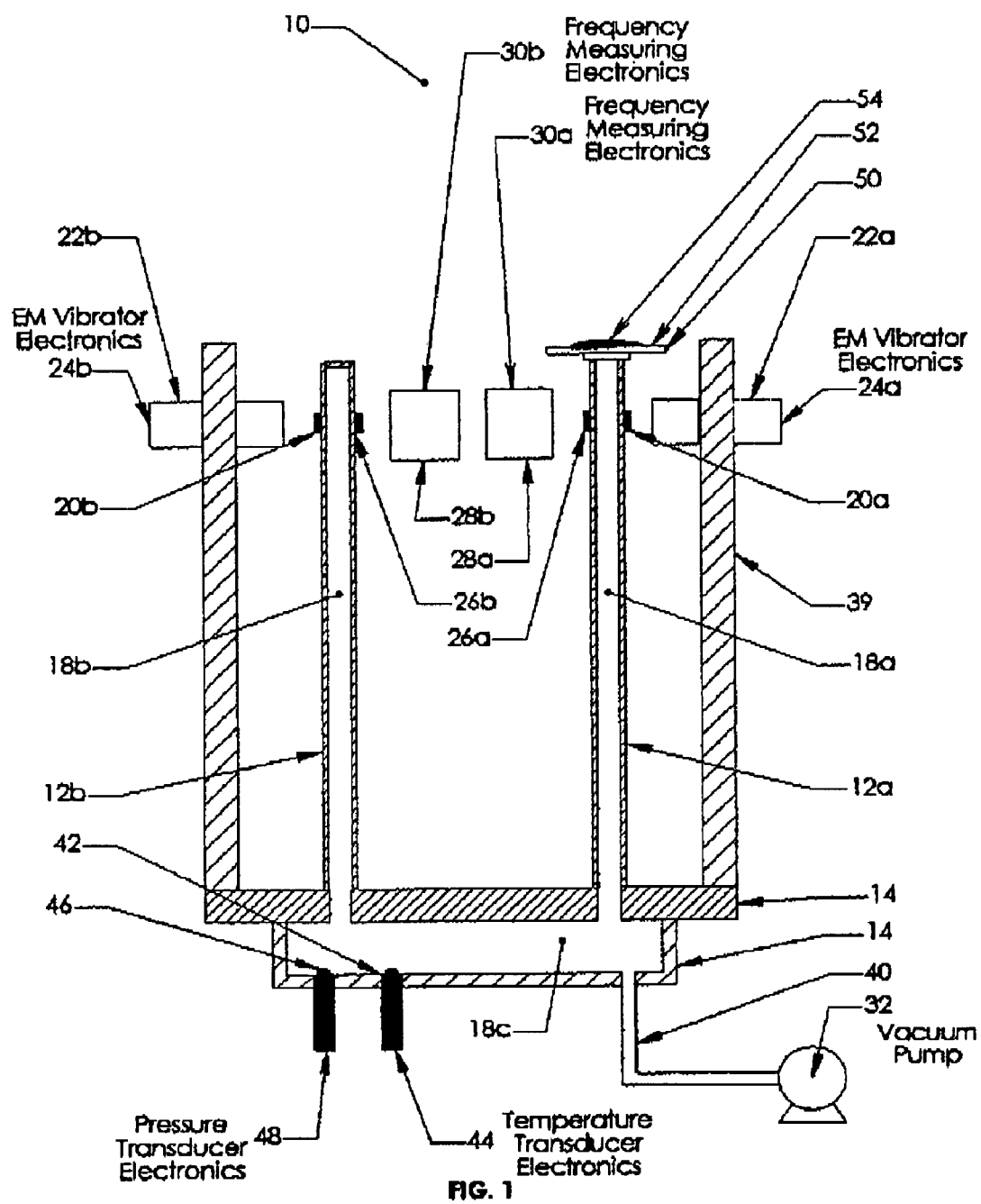
FIG. 1 is a section view of one embodiment of an idealized passively compensated microbalance showing an exemplary installation and related equipment.

The present invention provides for a passive method and apparatus which overcomes problems found in the prior art.

In several embodiments of the present invention there is no need to utilize complex methods and or formulae for the heat treatment of the oscillating element as illustrated in U.S. Pat. No. 6,080,939. Additionally, schemes such as those in U.S. Pat. No. 6,080,939 sport elastic oscillating elements with "low" thermoelastic coefficients that are not "low" enough to support the accuracy and resolution requirements of the subject invention. It is therefore important to select a material that exhibits low losses of energy per unit oscillation. Such systems are said to have a "High Q", and provide a passive means of removing the effects of a non zero thermoelastic coefficient.

The present invention significantly reduces the temperature sensitivity by utilizing a differential mode wherein two or more resonators are utilized and only one is subjected to the collected mass. This is often referred to as removing "common mode" errors. The "common mode" being those elements that change in a known predictable manner in both devices that can be easily subtracted from one another.

In harsh industrial environments a three axis accelerometer can be utilized to enable one to mathematically remove the adverse effects caused by external vibration. The methods of vibration compensation are well known in the art and are presently applied in vibration compensated sensors such as those detailed in U.S. Pat. No. 6,498,996 and many of the references cited in that patent as well as many optical related vibration compensation means, such as those described in U.S. Pat. No. 5,777,741 and references cited in that patent.

According to one aspect of the invention, the temperature sensitivity of an instrument, for example the microbalance as previously described, is reduced by maintaining the instrument, or at least a temperature-sensitive element thereof, at a constant temperature. This is achieved by: applying heat to the instrument; measuring a parameter that is indicative of the temperature of the instrument; and controlling the amount of heat applied to the instrument to maintain the measured parameter substantially constant.

While this process sounds simple to attain in practice, maintaining a constant temperature of a system that draws air into the filter is nearly impossible due to the fact that the sampled air may not have a sufficient "residence time" in the heated oscillating element tubes, or the inlets thereto, to attain the desired temperature. For example one could not expect to heat air from 20 Deg C. to 100 Deg C. in a 1 inch long soda straw. However, if the straw is 20 inches long the residence time for the air that the heating element has heat is sufficient.

One way this control may be accomplished is by affixing a resistive heater on the oscillating element of the microbalance. The resistive heater can be wound onto the oscillating element, vacuum deposited, or applied by any other means.

Some glass formulations allow embedding platinum heater windings directly within the glass. Radiant or other types of heating, such as convective and conductive, can also be employed. A radiant heater would be positioned appropriately next to or around the oscillating element to provide heat thereto. The parameter that is used to control the amount of heat supplied to the heater can be the resistance of the heating element (which is dependent on the temperature), or the output of an appropriately positioned temperature sensor. This method is addressed in U.S. Pat. No. 6,444,927.

Embodiments of the present invention serve to eliminate the need for active temperature control of the oscillating member by significantly reducing the temperature sensitivity. By employing a differential mode, wherein two resonators are utilized, and only one is subjected to the collected mass, the need to maintain the oscillating element at a constant temperature may be reduced or removed.

For example, consider two perfectly equal tuning forks in an environmental chamber that can change temperature and pressure. Assume both tuning forks remain free of any contamination or particulate. If we operate the environmental chamber (condition A) at a high pressure and low temperature the two tuning forks will resonate at the exact same rate of 410 Hz. The difference between them is ZERO. If we now lower the pressure and increase the heat (Condition B) the difference between the two tuning forks will again be ZERO but the frequency will now be 415 Hz. While the frequency went from 410 Hz to 415 Hz the DIFFERENCE was ZERO. This is the essence of a differential system, wherein the "common mode" error, the difference between 410 Hz and 415 Hz is removed by virtue of measuring the difference between two perfectly equal tuning forks. If one of the tuning forks has a 1 gram mass added to it the difference in frequency it exhibits, compared to the other tuning fork, would be solely indicative of the mass alone. This DIFFERENTIAL method allows the user to determine the mass on tuning fork in any reasonable condition.

For example, consider the same two tuning forks but now they are exactly the same except for their resonant frequencies being 410 Hz and 310 Hz at Condition A and exhibiting 415 Hz and 315 Hz at condition B. The difference at Condition A and Condition B is the same, thereby removing the "common mode" error thus illustrating that the two tuning forks do not need to be exactly the same in every respect. In this case we can conclude, and experiments agree with the theory, that the two elastic oscillating elements need only to be completely characterized in order to remove the "common mode" errors. This can even be shown to be true utilizing an elastic oscillating element described in this patent as well as a microstructure elastic oscillating element as described in U.S. Pat. No. 6,784,381 held by this applicant.

A further error in the use of microbalances having hollow oscillating elements is caused by temperature and/or pressure changes in the fluid located within the cavity of the hollow oscillating element.

As the temperature or pressure of the fluid within the cavity of the hollow oscillating element varies, so will the density of the fluid. Assuming that the interior volume of the cavity of the hollow oscillating element remains substantially constant, a variation in the density of the fluid will result in a variation of the mass of the fluid located in the cavity of the hollow oscillating element. That is, the effective mass of the oscillating element will vary with temperature and/or pressure changes in the fluid located therein. This variation in the effective mass of the oscillating element will in turn affect the resonant frequency of the oscillating element and indicate a change in mass when, in fact, the mass is constant.

Embodiments of the present invention significantly reduce the temperature and/or pressure sensitivity by employing a differential mode wherein two resonators are utilized and only one is subjected to the collected mass. Both resonators are in fluid communication with each other thereby removing the need to maintain the pressure and/or temperature of the fluid within the oscillating element constant or to compensate for those variables.

The pressure-dependent error frequently manifests itself as a perceived negative mass over time. As the filter element loads up with particulate or other forms of flow impeding elements, the pressure within the cavity of the hollow oscillating element will decrease due to the increased resistance of the filter element. As the pressure of the fluid decreases, so does the density, reducing the mass of the column of fluid within the cavity of the hollow oscillating element. This, in turn, will increase the resonant frequency of the oscillating element, indicating a false reduction in the mass of the filter element and its entrapped matter. These false reductions in mass readings plague prior art devices, such as those described in U.S. Pat. No. 4,391,388.

Similarly, if the fluid gets colder, the density of the fluid column in the cavity of the hollow oscillating element will increase, increasing the mass within the cavity of the hollow oscillating element. The resonant frequency of the oscillating element will be correspondingly lower, thereby indicating an erroneously high mass. The reverse is true if the fluid temperature increases.

By utilizing a differential mode, or "common mode", wherein two resonators are utilized and only one is subjected to the collected mass, we remove the need to maintain the pressure and/or temperature of the fluid within the oscillating element constant or to compensate for those variables.

Figure 2:
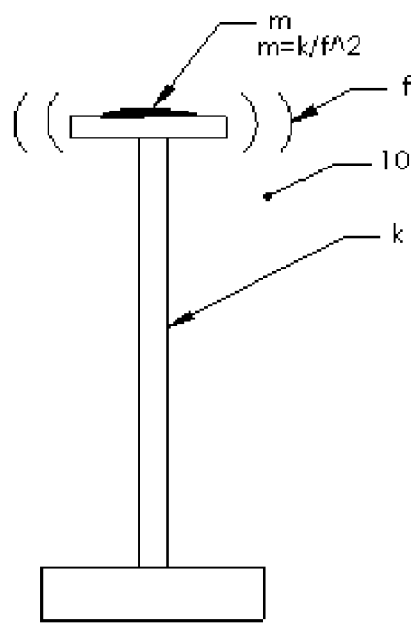
FIG. 2 is a side view of a classical single oscillating element microbalance illustrating the principles of operation thereto.

Referring to FIG. 2, the principle of operation of a single oscillating element microbalance 10 can be represented by $m = k/f^2$ where m is the mass in grams, f is the frequency in Hz, and k is the spring constant in $g*Hz^2$.

For a particular single oscillating element microbalance, the spring constant can be determined by using two values of m, one for "zero" mass (i.e. the system mass only), and one for an additional mass added to the "zero" mass. The system mass is of course not actually zero—we "tare" the system mass out for purposes of convenience much like a post office scale is zeroed before the letters are placed in a box on the scale. This ensures that the mass of the letters alone are considered, and not the mass of the box.

The equation for the spring constant can be derived as follows: $k = (m1 - m0)/(1/f1^2 - 1/f0^2)$ Using exemplary values of m1=0.075 g, m2=0, f1=250 Hz and f0=311.314 Hz yields a value of k=13,200 $g*HZ^2$. We can see that we can determine the spring constant, k, for two oscillating elements as well as one. We can mathematically combine these two spring constants and combine them to a new term such as Bulk K. The equation for the Bulk K is determined in much the same manner as above.

The actual system mass at this temperature can now be determined by substituting the determined value of k and the observed value of f for the "zero" mass condition. Using these two values, we arrive at a system mass of 0.136199 g.

Figure 3:
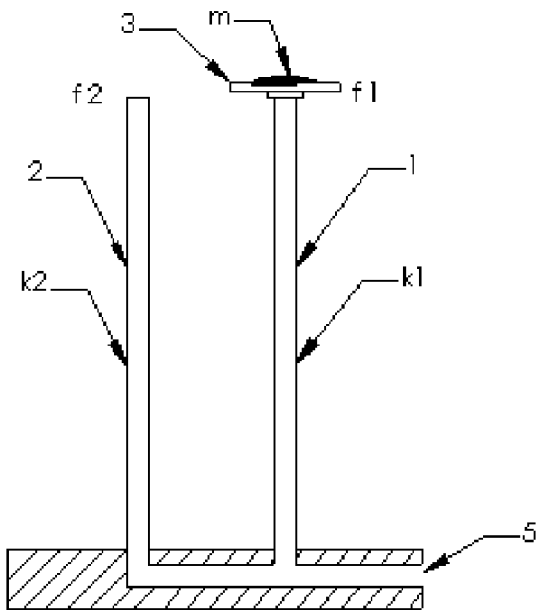
FIG. 3 is a simplified sectional side view of a microbalance in accordance with the present invention, illustrating the principles of operation thereto.

Referring now to FIG. 3 we see two hollow oscillating elements, 1 and 2. These two oscillating elements are excited into resonance utilizing methods well known in the art. Oscillating element 1, called the "collector", has a filter collection means 3 attached while oscillating element 2, called the "reference", has none. Both oscillating elements 1 and 2 are subjected to substantially the same operating environment including the pressure or vacuum within the hollow oscillating elements indicated at 5. As such we can determine a Bulk K value for the system comprised of two oscillating elements.

Figure 5:
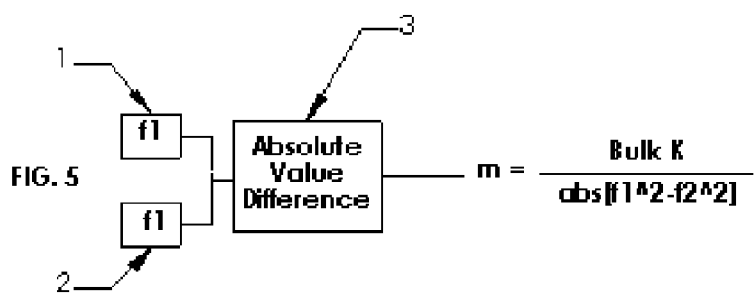
FIG. 5 is a schematic view showing the data processing of the signals to attain a passively corrected indication of the collected mass.

Referring now to FIG. 5, illustrated is a frequency measuring means commonly known in the art at 1 and 2. These two measured resonant frequency values come from the resonance of 1, the "collector", and the resonance of 2, the "reference". The absolute value of the square of the difference between 1 and 2 combined with the Bulk K results in an indication of the mass of the collected particulate without the errors contributed by changes in pressure, temperature, modulus of elasticity and even external vibration as all of these changes impact the resonance of both 1 and 2 equally. The "common mode" errors are removed and or minimized utilizing a differential arrangement as described in this patent.

Figure 4:
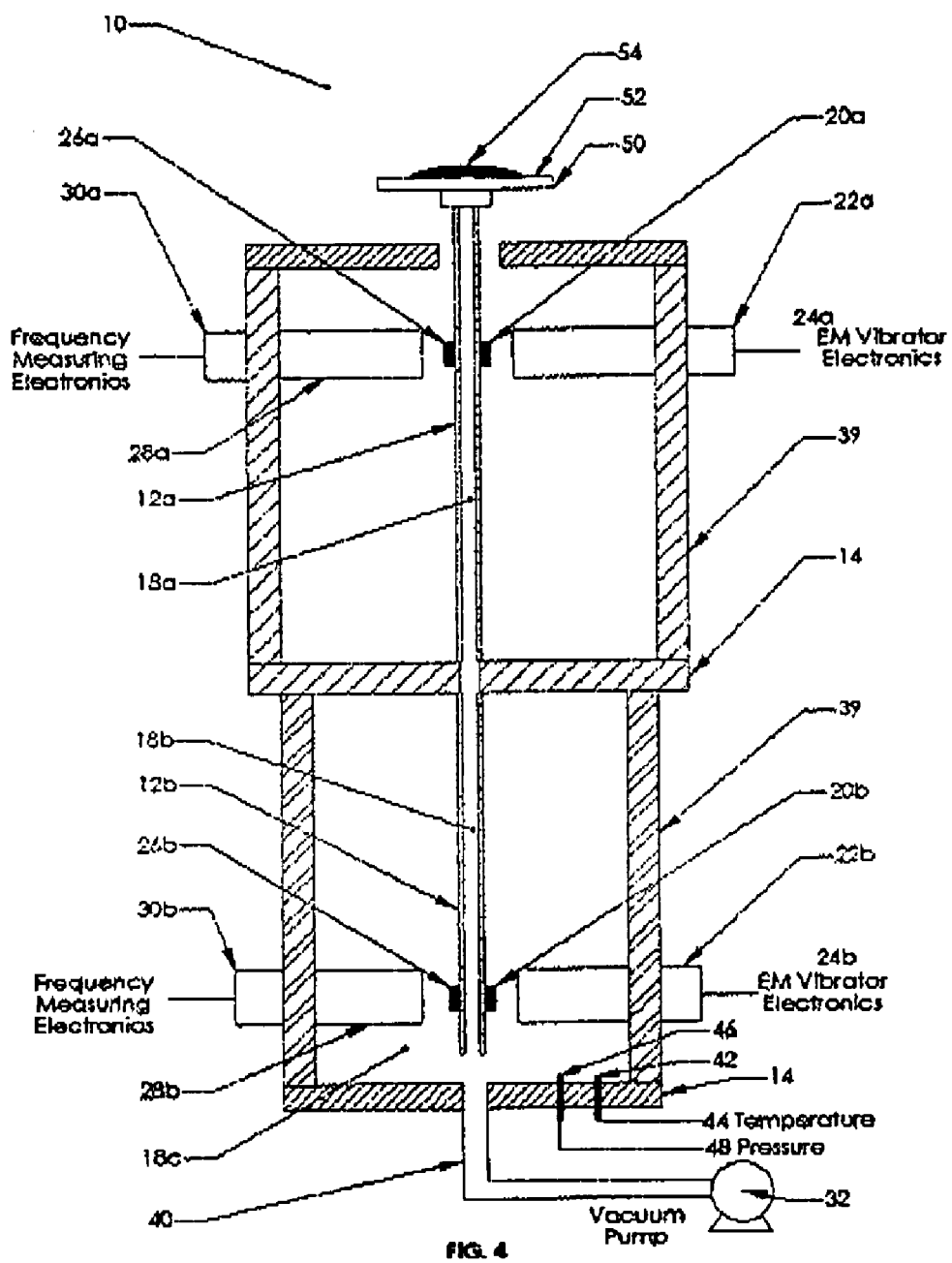
FIG. 4 is a section view of another embodiment of an idealized passively compensated microbalance showing an exemplary installation and related equipment.

Referring now to FIGS. 1 and 4, a microbalance 10 comprises two elastic oscillating elements 12a and 12b, an enclosure 39 and a base assembly 14.

The oscillating elements 12a and 12b may be made of known materials used in the manufacture of microbalances, but they may also be made of other materials such as nickel alloys, Ni-Span-C, Ni-Span-D, Inconel, quartz, and quartz-glass alloys. For example, a nickel-cobalt alloy may be used for its properties of increased strength and decreased temperature coefficient of elasticity. By applying the temperature compensation described herein, it is possible to use materials with less-restrictive temperature dependencies of the modulus of elasticity, since embodiments of the present invention reduce the sensitivity of the instrument to external temperature variations.

Additionally, the oscillating element 12 may be manufactured using the electroforming manufacturing method. The electroforming method is similar to the method utilized for chrome plating automobile bumpers except that an appropriately shaped form is used on which to plate the material. The use of electroforming materials from which to make the oscillating elements 12a and 12b will inherently result in the two oscillating elements being substantially equal in properties providing for simplified manufacturing methods to produce substantially equal thermoelastic coefficients yielding an ideal assembly for running the embodiments in a differential mode. Utilizing separate oscillating elements requires more demanding manufacturing methods to ensure both oscillating elements exhibit substantially the same thermoelastic coefficients, or are well characterized to enable mathematically correlating them to one another to enhance the quality of the "common mode" error reduction. Additionally, an electroformed oscillating element offers a lower temperature dependence over the normal operating temperature range of the system than many of the glass compositions available. This is because the change in Young's modulus of elasticity over temperature of the electroforming materials is typically a few orders of magnitude smaller than many of the available glass compositions. Additionally, oscillating elements made from an electroformed material are many times more rugged than glass elements, potentially lending the subject device to wider use.

Figure 6:
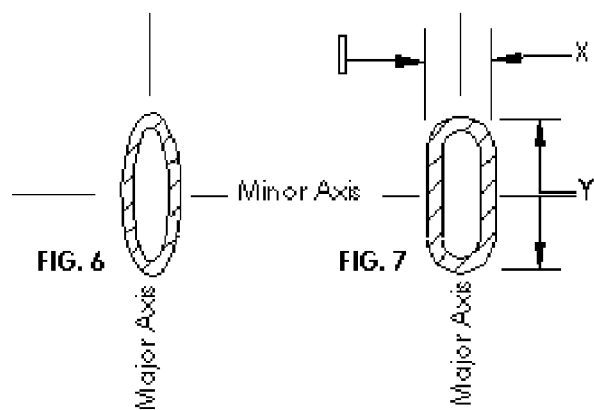
FIG. 6 is a sectional view, showing the ratio of the major axis to minor axis being at least 1.5:1, of elastic oscillating element of the microbalance of FIG. 1.
Figure 7:
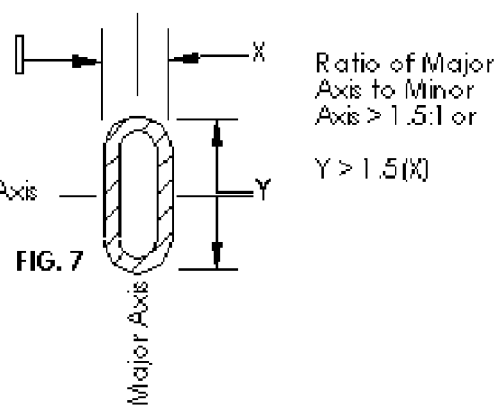
FIG. 7 is an alternate sectional view, showing the ratio of the major axis to minor axis being at least 1.5:1, of the elastic oscillating element of the microbalance of FIG. 1.

The oscillating elements 12a and 12b are mounted at one end thereof to the base assembly 14, and the other end thereof is free to vibrate. As can be seen in FIG. 6 and FIG. 7 the oscillating elements 12a and 12b can have an elliptical or race track cross-section in the illustrated embodiment, but other cross-sections may be used. The use of these cross sections results in the primary/lowest resonant frequency of the oscillating elements 12a and 12b being in a predictable path, that is, along the minor axis. It is also important to note that the commercial embodiments of oscillating elements described in U.S. Pat. No. 4,391,338, along with its variants, exhibit significant precession, or the inability to oscillate in a single plane. It is a simple matter to view the precession in prior art devices with a strobe light tuned to the resonant frequency. The precession is a result of the cross-section being more circular than elliptical or of a race track geometry. The prior art misses the extreme importance of maintaining at least a minimum ratio of the major axis to the minor axis. Our invention teaches that the ratio of the major axis to the minor axis should be at least 1.5:1. In order for all of the energy to be given to a single measurable axis it is therefore of paramount import to ensure that the elastic oscillating element resonates in a single plane. If the element precesses, as exhibited in observing the wobble of a non-ideal spinning top (where there exists an external force acting to cause precession), the measured frequency will not be solely from a single identifiable and measurable source. The energy that is given to precession will be indicative of errors in the resonant frequency. As such these errors will result in errors in the basic measurement allowing the calculation of the mass. The means for exciting the oscillating elements 12a and 12b, and for measuring the resulting vibration, are accordingly also located along the minor axis of the ellipse or race track.

Mounted towards the upper end of the oscillating elements 12a and 12b are discs 20a, and 20b of magnetic or iron alloy material that is used to couple the excitation force to the oscillating elements 12a and 12b when acted upon by electromagnets 22a and 22b (under control of EM vibrator electronics 24a and 24b.) Mounted to the oscillating elements 12a and 12b, opposite to the discs 20a and 20b, are magnetic or iron alloy discs 26a and 26b (typically the same as disc 20a and 20b) that under vibration of the oscillating elements 12a and 12b causes a fluctuation in the magnetic fields in electromagnets, or position sensing transducers, 28a and 28b, which is detected by frequency measuring electronics 30a and 30b. As the name suggests, the frequency measuring electronics 30a and 30b measure the individual resonant frequencies of the oscillating elements 12a and 12b of the microbalance 10. It will of course be appreciated that other structures and methods may be used for exciting the oscillating elements 12a and 12b and for measuring the resonant frequency of the oscillating elements 12a and 12b of the microbalance 10. For example, optical, capacitive, and piezoelectric or induction measuring devices, systems and methods may be used to measure the frequency of the oscillating elements 12a and 12b of the microbalance 10.

The oscillating elements 12a and 12b are hollow, with cavities 18a, 18b, and 18c that communicate to the vacuum pump 32, the pressure transducer 46, and the temperature transducer 42. It will be apparent that the temperatures within 18a, 18b, and 18c will be substantially equal, plus or minus three degrees Centigrade, because the same fluid condition exists in both resonators. It will also be apparent that the pressures within 18a, 18b, and 18c will be substantially equal, plus or minus a few tenths of a millimeter of mercury, because the same fluid condition exists in both resonators and the pressure drop is nearly zero. It is the property of the pressures and temperatures within 18a, 18b, and 18c being substantially equal that is paramount to the embodiments of the present invention and it is this property which allows the differential mode to successfully remove the adverse effects of temperature, pressure and changing modulus of elasticity with temperature. In use, a fluid is drawn through the oscillating element from the free end to the fixed end, and out through a passage defined in the base 14. As can be seen from FIGS. 1 and 4, this fluid flow is generated by a vacuum supply or pump 32 that is in fluid communication with the cavities 18a, 18b, and 18c.

Referring again to FIGS. 1 and 4, the base assembly 14 has cavity 18c defined therethrough and a connector 40 that provides a connection to which the vacuum supply or pump 32 can be connected. A temperature transducer 42 is mounted in the base assembly 14 with its sensitive element in communication with the cavity 18c. The temperature transducer 42, in conjunction with temperature transducer electronics 44, is used to determine the temperature of the fluid in the cavity 18c. Similarly, a pressure transducer 46 and associated pressure transducer electronics 48 are used to determine the pressure of the fluid in the cavity 18c. Cavity 18c includes the interior of the hollow oscillating elements 12a and 12b. (shown as 18a and 18b respectively). The temperature and pressure information in cavity 18c can be used to indicate and control the mass flow rate delivered by the vacuum pump 32 and/or a mass flow controller.

In an embodiment, a filter holder 50 is mounted to the free end of the oscillating element 12a. The filter holder 50 provides a fixture for positioning a replaceable filter 52 so that the fluid that is drawn into the oscillating element 12a passes through the filter 52. As the fluid is drawn through the filter, particulate matter 54 in the fluid becomes trapped in or on the filter 52. It is the measurement of the mass of the particulate matter 54 trapped by filter that is the purpose of the microbalance 10. It can be appreciated that the filter 52 must be firmly affixed to filter holder 50 to prevent the filter 52 from moving relative to the filter holder 50. This can be accomplished by securing the two elements together with any appropriate securing means (e.g. glue, epoxy or ultrasonic welding) compatible with the specific application. This inventor has a patent application in a place describing methods of manufacturing a filter and filter holder assembly that accomplishes these important features.

Figure 8:
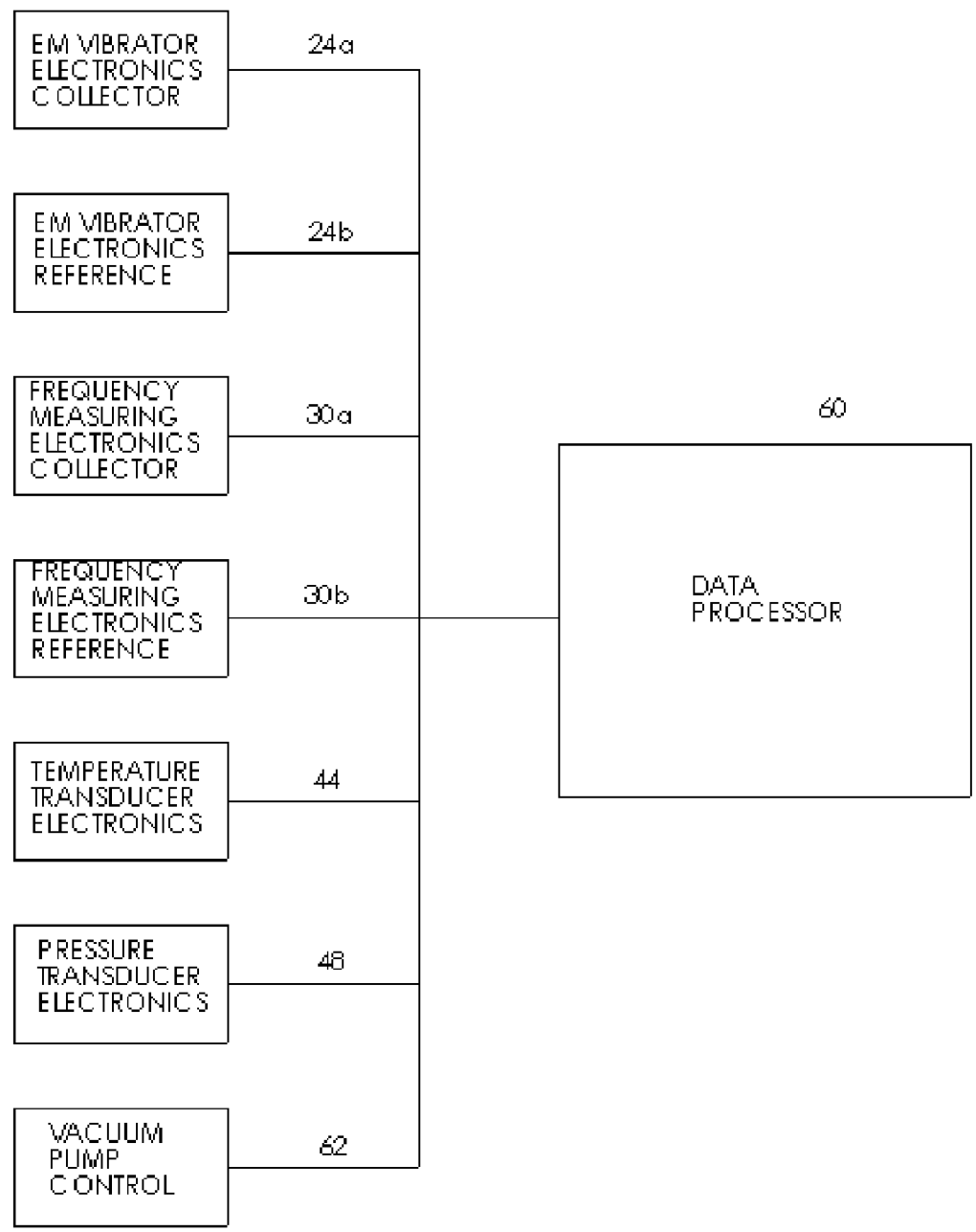
FIG. 8 is a schematic view of a data processor and related components with the microbalance of FIG. 1.

FIG. 8 shows an exemplary data-processing configuration that may be used with the microbalance described above. As shown in FIG. 8, a data processor 60 can be provided to receive information from and/or to control the various control electronics described above, as well as vacuum pump control electronics 62.

The data processor 60 may be a general-purpose computer or a dedicated microprocessor, or any other computing device having sufficient computing capabilities to operate the microbalance 10. It will also be appreciated that some or all of the control and computing functions shown separately in FIG. 8 may be integrated into one or more control or computing devices. Similarly, the particular interconnections between the devices may be varied, or may not be present at all. For example, the EM vibration electronics 24*a* and 24*b* and the vacuum pump control 62 may be freestanding units not connected to other units or the data processor 60.

The density of the fluid will be compensated for by the virtue of the fact that we are taking the difference of the frequencies of oscillating element 12*a* and 12*b* which compensates for the variation in density (mass) of the fluid in the cavity of the hollow oscillating elements 12*a* and 12*b* as previously described. Having both oscillators operating in a differential mode, with either nearly equal or known operating characteristics as well as a nearly equal fluid communication will provide for near ideal "common mode" error elimination and or reduction.

It can be appreciated that continuously measuring the resonant frequency of both oscillation elements provides for an indication of the mass in near real time without the possibility of missing "episodes" of minimum or maximum mass collection as is probable with current art systems.

There are clearly a variety of modifications that could be made to the above described invention without departing from its essential principles. It is intended that all such modifications be encompassed within the scope of the following claims.

What is claimed is:

1. An oscillating inertial microbalance comprising:
   a base assembly;
   an enclosure;
   a vacuum pump;
   a pressure transducer;
   a temperature transducer;
   two elastic oscillating elements substantially equal in properties mounted at one end of said base assembly;
   a filter accommodated on only one of said oscillating elements;
   a means for inducing resonance in said oscillating elements; and
   a means for measuring the resulting vibrations;
   wherein the pressures and temperature within the cavities of said oscillating elements are maintained substantially equal and wherein the mass of a particulate collected on said filter is measured by performing the steps of:
   forcing said oscillating elements into resonance, continuously measuring the frequency of each of said oscillating elements and computing the collected mass in near real time.

2. The oscillating inertial microbalance of claim 1 wherein said oscillating elements are selected from the following group: nickel alloys, Ni-Span-C, Ni-Span-D, Inconel, quartz, and quartz-glass alloys.

3. The oscillating inertial microbalance of claim 1 wherein the ratio of the major axis to the minor axis of the elastic oscillating elements is at least 1.5:1 to reduce precession.

4. The oscillating inertial microbalance of claim 1 wherein the value for the collected mass is derived from any combination of the pressure, temperature, or acceleration measurements.

5. The oscillating inertial microbalance of claim 1 wherein said two elastic oscillating elements are not fabricated of the same material and are not equal in mechanical configuration.

6. The oscillating inertial microbalance of claim 1 further comprising a data processor for receiving and sending data to and from one or more components of said microbalance.

7. A method of operating a microbalance, the microbalance including two hollow inertial oscillating elements with substantially equal properties and with only one having a filter mounted at one end thereof, comprising: inducing resonance in said oscillating elements; measuring the frequency of each of said oscillating elements; and utilizing the results of the data derived from each resonator to allow for computation of the mass.

8. The method of operating a microbalance of claim 7 wherein said oscillating elements are selected from the following group: nickel alloys, Ni-Span-C, Ni-Span-D, Inconel, quartz, and quartz-glass alloys.

9. The method of operating a microbalance of claim 7 wherein the ratio of the major axis to the minor axis of the elastic oscillating elements is at least 1.5:1 to reduce precession.

10. The method of operating a microbalance of claim 7 wherein the data is derived from the pressure, temperature and acceleration are measured.

11. The method of operating a microbalance of claim 7 wherein said two elastic oscillating elements are not fabricated of the same material and are not equal in mechanical configuration.

12. The method of operating a microbalance of claim 7 wherein said microbalance further comprises a data processor for receiving and sending data to and from one or more components of said microbalance.

* * * * *